United States Patent
Alzaher et al.

(10) Patent No.: US 9,564,874 B1
(45) Date of Patent: Feb. 7, 2017

(54) ULTRA-LOW FREQUENCY BIO-MEDICAL ACTIVE-RC LOWPASS FILTERS

(71) Applicant: KING FAHD UNIVERSITY OF PETROLEUM AND MINERALS, Dhahran (SA)

(72) Inventors: Hussain Abdullah Alzaher, Dhahran (SA); Mohammad Khalaf Alghamdi, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 14/843,646

(22) Filed: Sep. 2, 2015

(51) Int. Cl.
| | | |
|---|---|---|
| H03K 5/00 | (2006.01) |
| H03H 11/12 | (2006.01) |
| A61B 5/00 | (2006.01) |
| H03H 11/04 | (2006.01) |

(52) U.S. Cl.
CPC ......... H03H 11/1256 (2013.01); A61B 5/7225 (2013.01); H03H 11/04 (2013.01); H03H 11/1213 (2013.01)

(58) Field of Classification Search
CPC . H03H 11/0422; H03H 11/04; H03H 11/1291; H03H 11/1213; H03K 5/1252
USPC .................................................. 327/551–559
See application file for complete search history.

(56) References Cited

U.S. PATENT DOCUMENTS

| 7,279,962 | B2 | 10/2007 | Chen et al. | |
|---|---|---|---|---|
| 8,120,417 | B2* | 2/2012 | Kannan | H03F 3/45183 327/552 |
| 8,436,679 | B1* | 5/2013 | Alzaher | H03H 11/1256 327/556 |
| 8,952,748 | B2* | 2/2015 | Guimaraes | H01L 28/40 327/554 |
| 9,077,585 | B2* | 7/2015 | Alzaher | H04L 25/063 |

OTHER PUBLICATIONS

Alzaher, H., et al., "Enhancing Low frequency Operation of Active-RC Filters Employing R-2R Networks", IEEE, pp. 147-151, Isbn: 978-1-4673-5613-8©, (2013).
Mahnashi, Y., et al., "Applying the Difference Term Approach for Low Frequency Biomedical Filter", J Biosens Bioelectron, pp. 1-3, URL: http://www.omicsonline.org/2155-6210/2155-6210-S11-004. digital/2155-6210-S11-004.html, (2012).

* cited by examiner

Primary Examiner — Dinh T Le
(74) Attorney, Agent, or Firm — Oblon, McClelland, Maier & Neustadt, L.L.P.

(57) ABSTRACT

Active-RC low-pass filters based on R-0.5R ladders are implemented to provide high linear and low power design solutions for integrated biomedical applications. Among various R-αR ladders family, R-0.5R ladders provide the best low frequency selectivity characteristics. The filters exhibit ultra-low pole frequencies and occupy relatively compact silicon areas by using the R-0.5R ladders.

12 Claims, 10 Drawing Sheets

ULTRA-LOW FREQUENCY BIO-MEDICAL ACTIVE-RC LOWPASS FILTERS

FIELD

Exemplary embodiments described herein relate to ultra-low frequency bio-medical active-RC low pass filters.

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Design of high quality biomedical devices to gather real-time physiologic parameters from a patient body could be the key point in saving the patient's life. These devices monitor biomedical signals in order of volts, V, to mV at the body surface and hence are susceptible to noise and interference. Low power, highly linear analog filters have wide range of applications in biomedical signal processing for example, a hearing aid as described in I. Deligoz, S. R. Naqvi, T. Copani, S. Kiaei, B. Bakkaloglu, S. Je, and J. Chae, ("A MEMS-based power-scalable hearing aid analog front end," IEEE Tran. on Biomed. Circ. and Syst., vol. 5, no. 3, pp. 201-213, June 2011—incorporated herein by reference), photoplethysmogram as described in A. Wong, K. Pun, Y. Zhang, and K. Nang Leung, ("A low-power CMOS front-end for photoplethysmographic signal acquisition with robust DC photocurrent rejection," IEEE Tran. on Biomed. Circ. and Syst., vol. 2, no. 4, pp. 280-288, December 2008—incorporated herein by reference), electrocardiogram (ECG) as described in S. Lee, and C. Cheng, "Systematic design and modeling of a OTA-C filter for portable ECG detection," IEEE Tran. on Biomed. Circ. and Syst., vol. 3, no. 1, pp. 53-64, February 2009—incorporated herein by reference), wearable breathing detector as described in P. Corbishley and E. Rodriguez-Villegas, ("A nanopower bandpass filter for detection of an acoustic signal in a wearable breathing detector." *IEEE Tran. on Biomed. Circ. and Syst.*, vol. 1, no. 3, pp. 163-171, 2007—incorporated herein by reference), pulse oximeter as described in K. Li and S. Warren, "A wireless reflectance pulse oximeter with digital baseline control for unfiltered photoplethysmograms," *IEEE Tran. on Biomed. Circ. and Syst.*, vol. 6, no. 3, pp. 269-278, June 2012—incorporated herein by reference), acquisition of various neurophysiological signals as described in M. Mollazadeh, K. Murari, G. Cauwenberghs, and N. Thakor, ("Micropower CMOS integrated low-noise amplification, filtering, and digitization of multimodal neuropotentials," *IEEE Tran. on Biomed. Circ. and Syst.*, vol. 3, no. 1, pp. 1-10, February 2009—incorporated herein by reference) and M. Mollazadeh, K. Murari, G. Cauwenberghs, and N. Thakor, "Wireless micropower instrumentation for multimodal acquisition of electrical and chemical neural activity," IEEE Tran. on Biomed. Circ. and Syst., vol. 3, no. 6, pp. 388-397, December 2009—incorporated herein by reference), neural spike detection as described in A. Rodríguez-Pérez, J. Ruiz-Amaya, M. Delgado-Restituto, and Á. Rodríguez-Vázquez, "A low-power programmable neural spike detection channel with embedded calibration and data compression," IEEE Tran. on Biomed. Circ. and Syst., vol. 6, no. 2, pp. 87-100, April 2012—incorporated herein by reference), EEG monitoring as described in R. F. Yazicioglu, P. Merken, R. Puers, and C. V. Hoof, ("A 200 uW eight-channel EEG acquisition ASIC for ambulatory EEG systems," IEEE J. Solid-State Circuits, vol. 43, no. 12, pp. 3025-3038, December 2008—incorporated herein by reference), and neural recording systems as described in A. Wong, K. Pun, Y. T. Zhang, and K. Hung, ("A near-infrared heart rate measurement IC with very low cutoff frequency using current steering technique," IEEE Trans. Circuits Syst. I, vol. 52, no. 12, pp. 2642-2647, December 2005-incorporated herein by reference).

However, as recognized by the present inventor, designing ultra-low frequency filters for biomedical signal processing is a challenging problem due to the difficulty in developing efficient methods achieving large time constant while maintaining high linearity performance.

SUMMARY

In one embodiment, there is provide a R-αR ladder active-RC low pass filter with reduced lower pole frequencies for high linear and low power bio-medical applications, comprising: a first inverting input terminal; a second non-inverting input terminal; a first inverting output terminal; a second non-inverting output terminal; first and second operational amplifiers connected together in a Tow-Thomas biquadratic filter circuit; a first R-αR ladder circuit connected between the first non-inverting input terminal of the low-pass filter and a third inverting input terminal of the first operational amplifier; a second R-αR ladder circuit connected between the second inverting input terminal of the low-pass filter and a non-inverting input terminal of first operational amplifier; a third R-αR ladder circuit connected in parallel with a first capacitor, wherein the third R-αR ladder circuit is connected between the third inverting input terminal and a third non-inverting output terminal of the first operational amplifier; a fourth R-αR ladder circuit connected in parallel with a second capacitor, wherein the fourth R-αR ladder is connected between the fourth non-inverting input terminal and a fourth inverting output terminal of the first operational amplifier; a fifth R-αR ladder circuit connected between the third non-inverting output terminal of the first operational amplifier and a fifth inverting input terminal of a second operational amplifier; a sixth R-αR ladder circuit connected between the fourth inverting output terminal of the first operational amplifier and a sixth non-inverting input terminal of the second operational amplifier; a seventh R-αR ladder circuit connected between the third inverting input terminal of the first operational amplifier and a sixth inverting output terminal of the second operational amplifier, wherein the sixth inverting output terminal is connected to the second inverting output terminal of the low-pass filter; and an eighth R-αR ladder circuit connected between the fourth non-inverting input terminal of the first and a fifth non-inverting input terminal of the second operational amplifier, wherein the fifth non-inverting output terminal is connected to the first non-inverting output terminal of the low-pass filter.

In another embodiment, the filter having an α value of 0.5 reduces a silicon area occupied by the filter, compared with the filter having other α values that are greater than 0.5 especially α=2, to implement the filter at a given pole frequency.

In another embodiment, the filter having an α value of 0.5 provides improvement in selectivity characteristics while consuming comparable power consumption, compared with another filter having another α value.

In another embodiment, equivalent maximum resistances of 2-stage, 3-stage, 4-stage, 5-stage, 6-stage, 7-stage, 8-stage, 9-stage, 10-stage, 11-stage and 12-stage R-αR ladder network are set as:

$$R_{eq}(2\text{-stages}) = (1 + 0.5\alpha)2R$$

$$R_{eq}(3\text{-stages}) = (1 + 2.5\alpha + 0.5\alpha^2)\frac{2R}{\alpha}$$

$$R_{eq}(4\text{-stages}) = [1 + 4.5\alpha + 4.5\alpha^2 + 0.5\alpha^3]\frac{2R}{\alpha^2}$$

$$R_{eq}(5\text{-stages}) = [1 + 6.5\alpha + 12.5\alpha^2 + 7\alpha^3 + 0.5\alpha^4]\frac{2R}{\alpha^3}$$

$$R_{eq}(6\text{-stages}) = [1 + 8.5\alpha + 24.5\alpha^2 + 27.5\alpha^3 + 10\alpha^4 + 0.5\alpha^5]\frac{2R}{\alpha^4}$$

$$R_{eq}(7\text{-stages}) = [1 + 10.5\alpha = 40.5\alpha^2 + 70\alpha^3 + 52.5\alpha^4 + 13.5\alpha^5 + 0.5\alpha^2]\frac{2R}{\alpha^5}$$

$$R_{eq}(8\text{-stages}) = [1 + 12.5\alpha + 60.5\alpha^2 +$$
$$142.5\alpha^3 + 168\alpha^4 + 91\alpha^2 + 17.5\alpha^2 + 0.5\alpha^7]\frac{2R}{\alpha^6}$$

$$R_{eq}(9\text{-stages}) = [1 + 14.5\alpha + 84.5\alpha^2 +$$
$$253\alpha^3 + 412.5\alpha^4 + 357\alpha^5 + 147\alpha^6 + 22\alpha^7 + 0.5\alpha^8]\frac{2R}{\alpha^7}$$

$$R_{eq}(10\text{-stages}) = [1 + 16.5\alpha + 112.5\alpha^2 + 409.5\alpha^3 +$$
$$858\alpha^4 + 1039.5\alpha^5 + 693\alpha^6 + 225\alpha^7 + 27\alpha^8 + 0.5\alpha^9]\frac{2R}{\alpha^8}$$

$$R_{eq}(11\text{-stages}) = [1 + 18.5\alpha + 144.5\alpha^2 + 620\alpha^3 + 1592.5\alpha^4 +$$
$$2502.5\alpha^5 + 2359.5\alpha^6 + 1254\alpha^7 + 330\alpha^8 + 32.5\alpha^9 + 0.5\alpha^{10}]\frac{2R}{\alpha^9}$$

$$R_{eq}(12\text{-stages}) = [1 + 20.5\alpha + 180.5\alpha^2 + 892.5\alpha^3 + 2720\alpha^4 + 5278\alpha^5 +$$
$$6506.5\alpha^6 + 4933.5\alpha^7 + 2145\alpha^8 + 467.5\alpha^9 + 38.5\alpha^{10} + 0.5\alpha^{11}]\frac{2R}{\alpha^{10}}$$

wherein $R_{eq}$(2-stages) is an equivalent maximum resistance of a two-stage R-αR ladder network, $R_{eq}$(3-stages) is an equivalent maximum resistance of a three-stage R-αR ladder network, $R_{eq}$(4-stages) is an equivalent maximum resistance of a four-stage R-αR ladder network, $R_{eq}$(5-stages) is an equivalent maximum resistance of a five-stage R-αR ladder network, $R_{eq}$(6-stages) is an equivalent maximum resistance of a six-stage R-αR ladder network, $R_{eq}$(7-stages) is an equivalent maximum resistance of a seven-stage R-αR ladder network, $R_{eq}$(8-stages) is an equivalent maximum resistance of an eight-stage R-αR ladder network, $R_{eq}$(9-stages) is an equivalent maximum resistance of a nine-stage R-αR ladder network, $R_{eq}$(10-stages) is an equivalent maximum resistance of a ten-stage R-αR ladder network, $R_{eq}$(11-stages) is an equivalent maximum resistance of a eleven-stage R-αR ladder network, and $R_{eq}$(12-stages) is an equivalent maximum resistance of a eleven-stage R-αR ladder network.

In another embodiment, the filtering having 12-stage R-0.5R ladders to obtain a lowest operational frequency with a minimum area.

In another embodiment, there is provided another R-αR ladder active-RC low pass filter to reduce lower pole frequencies for a high linear and low power bio-medical applications, comprising: a first input terminal; a first output terminal; a first ground node; a first R-αR ladder connected between the first input terminal and a second inverting input terminal of a first operational amplifier, wherein a second R-αR ladder parallel connected with a first capacitor, wherein the second R-αR ladder is connected between the first output terminal and the second inverting input terminal of the first operational amplifier, the second output terminal of the first operational amplifier is connected to the first output terminal, and a third non-inverting input terminal of the first operational amplifier is connected to a ground node.

In another embodiment employing 3-stage R-αR, wherein transfer function, gain and pole frequency of the filter are set as:

$$\frac{V_o}{V_i} = \frac{-1}{sCR\left(\frac{2+5\alpha+\alpha^2}{\alpha} + \frac{1}{A}\frac{2+5\alpha+\alpha^2}{\alpha}\right) + 1 + \frac{2}{A}\frac{(2+5\alpha+\alpha^2)}{\alpha^2}}$$

$$|A_{o3}| = \frac{1}{1 + \frac{2}{A}\frac{(2+5\alpha+a^2)}{\alpha^2}}$$

$$\omega_{o3} = \frac{1 + \frac{2}{A}\frac{(2+5\alpha+\alpha^2)}{\alpha^2}}{CR\left(\frac{2+5\alpha+\alpha^2}{\alpha}\right)\left(1 + \frac{1}{A}\right)}$$

wherein $V_i$ is a input voltage of the filter, $V_o$ is a output voltage of the filter, $A_{o3}$ is a gain of the filter, $\omega_{o3}$ is a pole frequency of the filter, C is the capacitance of the first capacitor and A is a gain of the operational amplifier.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
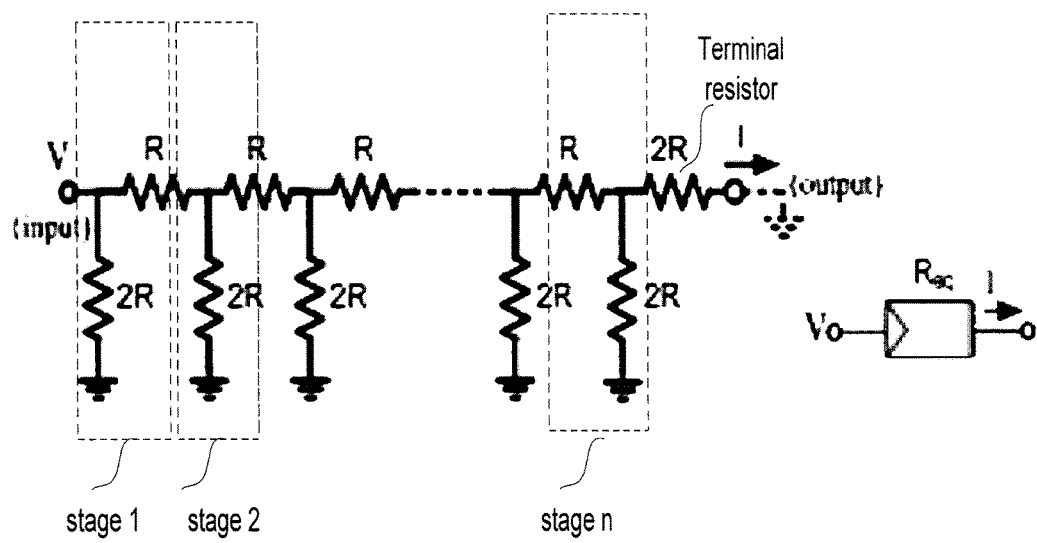
FIG. 1 is an exemplary circuit schematic of a R-2R ladder with a maximum resistance.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "about," and similar terms generally refer to ranges that include the identified value within a margin of 20%, 10%, or preferably 5%, and any values therebetween.

Some of the techniques used in the literature for designing very low frequency biomedical circuits are a MOS pseudo resistor, small transconductance OTA design, current steering/cancellation and impedance scaling as described in A. Wong, K. Pun, Y. T. Zhang, and K. Hung, ("A near-infrared heart rate measurement IC with very low cutoff frequency using current steering technique," *IEEE Trans. Circuits Syst. I*, vol. 52, no. 12, pp. 2642-2647, December 2005—incorporated herein by reference), S. Solis-Bustos, J. Silva-Martinez, F. Maloberti, and E. Sanchez-Sinencio, ("A 60 dB dynamic-range CMOS sixth-order 2.4 Hz low-pass filter for medical applications," IEEE Trans. Circuits Syst. II, vol. 47, no. 12, pp. 1391-1398, December 2000—incorporated herein by reference), C. Chen, P. Mak, T. Zhang, M. Vai, P. Mak, S. Pun, F. Wan, R. P. Martins, ("A 2.4 Hz-to-10 kHz-tunable biopotential filter using a novel capacitor multiplier," Asia Pacific Conference on Postgraduate Research in Microelectronics & Electronics (Prime Asia 2009), China, pp. 372-375, January 2009—incorporated herein by reference), C. L. Hsu, M. H. Ho, Y. K. Wu, and T. H. Chen, ("Design of low frequency low-pass filters for biomedical applications," in *Proc. Asia Pacific Conf. IEEE Circuits Systems*, Singapore, 2006, pp. 690-695—incorporated herein by reference).

A current steering circuit (using linearized MOSFET resistors) is used for designing a 2nd order lowpass filter for heart rate measurement. It is based on an operational amplifier and achieves a cutoff frequency of 18 Hz. Although this technique is effective in capacitance reduction, current steering transistors exhibit a nonlinear effect, as they suffer from a linearity problem with a decrease in frequency. The filter uses dual output linearized OTAs based on a series parallel approach together with capacitor scaling to realize a 3.8 Hz current mode 2nd order low-pass filter using leapfrog topology.

A fully integrated notch filter exhibiting high linearity and low power consumption was presented in H. Alzaher, N. Tasadduq, and Y. Mahnashi, "A Highly Linear Fully Integrated Powerline Filter for Biopotential Acquisition Systems," *IEEE Trans. on Biomedical Circuits and Syst.*, vol. 7, pp. 703-712, October 2013—incorporated herein by reference). High filter linearity is preserved utilizing an active-RC approach while IC implementation is obtained by replacing passive resistors with R-2R ladders to save area. The optimum design of a 50/60 Hz notch is achieved using 12 stage R-2R ladders. But, the number of stages for R-2R needs to be increased or the base resistance needs to be increased to a very high value, when the filter is required to further reduce the pole frequency. The further reduction of the pole frequency can lead to unacceptable filter area particularly for ultra-low pole frequency. A disclosed filter can obtain lower cut-off frequency while maintaining minimal area requirements.

FIG. 1 is an exemplary schematic of an R-2R ladder with maximum resistance. The R-2R ladder includes n cells of a resistance network. A series and a shunt resistance network are arranged in cascade to generate a voltage-to-current conversion. The series resistors of stages from 1 to n have a resistance of R. The terminal resistor has a resistance of 2R. The shunt resistors for all the stages have a resistance of 2R, with a first terminal of each shunt resistor being connected to the series resistor in the same stage, and a second terminal of each shunt resistor being connected to the ground. The R-2R ladders, which are conventionally used in data converters, are capable of achieving a large time constant because their equivalent resistance is much greater than their total actual resistance. They preserve the high linearity by using poly resistors and maintain zero DC power consumption. The largest possible equivalent resistance is achieved when only the least significant branch current (ILS) is connected to the virtual ground as shown in FIG. 1.

The maximum resistance $R_{eq(max)}=2^n R$ can be increased by increasing the size of the ladder (n) and/or the value of the basic resistance R. In this case there is no need to use any switch, and a huge silicon area is avoided, as well as associated manufacture voids, because of switch-on-resistances. The total area needed to implement an n-stage R-2R ladder would be that of $R_{tot}=(3n-1)R$. Since a silicon area that is occupied by a resistor is proportional to a resistance value of the resistor, a resistor with a smaller resistance value occupies less silicon area than a silicon area that occupied by a same-type of resistor with a larger resistance value. Accordingly, R and area have a direct relationship in this context. The reduction of the silicon area is obtained through the use of a R-2R ladder that is proportional to $R_{eq(max)}/R_{tot}$, which is $2^n/(3n-1)$. Therefore, the saving is independent of R values and improves considerably as n increases. The R-2R ladder can be used to provide huge resistance particularly when the number of stages is increased. A large R-2R ladder equivalent resistance can be achieved using a relatively small passive resistance. For example, for a 10 stage R-2R ladder with R=10 kΩ, equivalent resistance as high as 10 MΩ can be achieved while requiring an actual resistance of only 300 kΩ.

The R-2R ladder is used in data converters because it provides weighted values of resistance (R, 4R, 8R . . . $2^n$R) which are essential to fulfill the requirements of digital-to-analog (DAC) algorithms. On the other hand, such algorithm is not important when simulating high resistance. So instead of using R-2R, a general ladder R-αR with α as the index is described in
H. Alzaher, N. Tasadduq, Y. Mahnashi, ("Enhancing low frequency operation of active-RC filters employing R-2R networks," International Conference on Technological Advances in Electrical, Electronics and Computer Engineering (TAEECE), pp. 147-151, May 2013—incorporated herein by reference). As α is decreased, $R_{eq(max)}$ increases. Therefore, $R_{tot}$ decreases for the same number of stages and significantly less area is obtained. The general analytical expressions for $R_{eq(max)}$ as function of α and n for different ladder sizes are given by:

$$R_{eq}(2\text{-stages}) = (1+0.5\alpha)2R \tag{1}$$

$$R_{eq}(3\text{-stages}) = (1 + 2.5\alpha + 0.5\alpha^2)\frac{2R}{\alpha} \tag{2}$$

$$R_{eq}(4\text{-stages}) = [1 + 4.5\alpha + 4.5\alpha^2 + 0.5\alpha^3]\frac{2R}{\alpha^2} \tag{3}$$

$$R_{eq}(5\text{-stages}) = [1 + 6.5\alpha + 12.5\alpha^2 + 7\alpha^3 + 0.5\alpha^4]\frac{2R}{\alpha^3} \tag{4}$$

$$R_{eq}(6\text{-stages}) = [1 + 8.5\alpha + 24.5\alpha^2 + 27.5\alpha^3 + 10\alpha^4 + 0.5\alpha^5]\frac{2R}{\alpha^4} \tag{5}$$

$$R_{eq}(7\text{-stages}) = [1 + 10.5\alpha + 40.5\alpha^2 + 70\alpha^3 + 52.5\alpha^4 + 13.5\alpha^5 + 0.5\alpha^6]\frac{2R}{\alpha^5} \tag{6}$$

$$R_{eq}(8\text{-stages}) = [1 + 12.5\alpha + 60.5\alpha^2 + 142.5\alpha^3 + 168\alpha^4 + 91\alpha^5 + 17.5\alpha^6 + 0.5\alpha^7]\frac{2R}{\alpha^6} \tag{7}$$

$$R_{eq}(9\text{-stages}) = [1 + 14.5\alpha + 84.5\alpha^2 + 253\alpha^3 + 412.5\alpha^4 + 357\alpha^5 + 147\alpha^6 + 22\alpha^7 + 0.5\alpha^8]\frac{2R}{\alpha^7} \tag{8}$$

$$R_{eq}(10\text{-stages}) = [1 + 16.5\alpha + 112.5\alpha^2 + 409.5\alpha^3 + 858\alpha^4 + 1039.5\alpha^5 + 693\alpha^6 + 225\alpha^7 + 27\alpha^8 + 0.5\alpha^9]\frac{2R}{\alpha^8} \tag{9}$$

$$R_{eq}(11\text{-stages}) = [1 + 18.5\alpha + 144.5\alpha^2 + 620\alpha^3 + 1592.5\alpha^4 + 2502.5\alpha^5 + 2359.5\alpha^6 + 1254\alpha^7 + 330\alpha^8 + 32.5\alpha^9 + 0.5\alpha^{10}]\frac{2R}{\alpha^9} \tag{10}$$

$$R_{eq}(12\text{-stages}) = [1 + 20.5\alpha + 180.5\alpha^2 + 892.5\alpha^3 + 2720\alpha^4 + 5278\alpha^5 + 6506.5\alpha^6 + 4933.5\alpha^7 + 2145\alpha^8 + 467.5\alpha^9 + 38.5\alpha^{10} + 0.5\alpha^{11}]\frac{2R}{\alpha^{10}} \tag{11}$$

A circuit simulator can be used to determine $R_{eq(max)}$ for specific α and n by finding the ratio V/I as per shown in FIG. 1. Table I gives the corresponding numerical values of the normalized $R_{eq(max)}$/R for several different α and n as obtained from T-SPICE. These values are identical to their counterparts calculated using equations (1) through (11).

Figure 2:
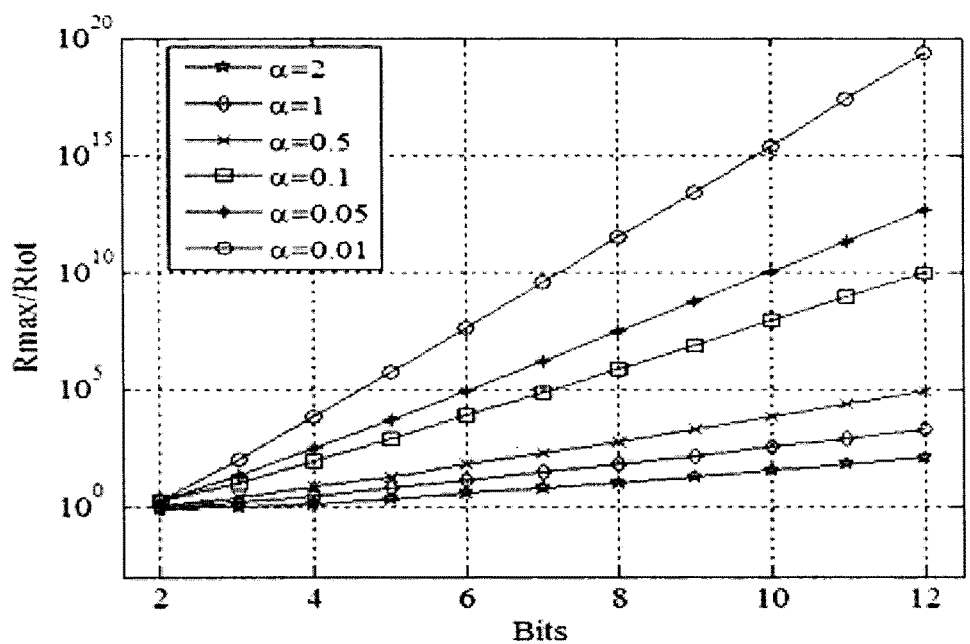
FIG. 2 is an exemplary graph of relative area saving as a function of a in R-αR ladder circuits.

FIG. 2 shows $R_{eq(max)}/R_{tot}$ as function of number stages of the R-αR ladder and index α. As the number of stages increase, the area reduces for all α. For 4 stage R-αR ladders, the reduction in area is 54.54% when α is changed from 2 to 0.5. While for 12 stage R-αR ladders, the area reduction is increased to 99.88% when α is changed from 2 to 0.5. Moreover, as the index α decreases, the reduction in area increases significantly for every given stage. For example, more area saving is obtained from 3 stage R-0.01R ladder compared with 12-stage R-2R ladder.

TABLE I

Numerical values of the normalized $R_{eq(max)}$/R

| Stages | R-2R | R-1R | R-0.5R | R-0.1R | R-0.05R | R-0.01R |
|---|---|---|---|---|---|---|
| 2 | 4 | 3 | 2.5 | 2.1 | 2.05 | 2.01 |
| 3 | 8 | 8 | 9.5 | 25.1 | 45.05 | 205.01 |
| 4 | 16 | 21 | 35.5 | 299.1 | 989.05 | 20909.01 |
| 5 | 32 | 55 | 132.5 | 3564 | 21714.5 | 2132550 |
| 6 | 64 | 144 | 494.5 | 42470 | 476725 | 217505 × 10³ |
| 7 | 128 | 377 | 1845.6 | 506075 | 10466 × 10³ | 2218275 × 10⁴ |

TABLE I-continued

Numerical values of the normalized $R_{eq(max)}/R$

| Stages | R-2R | R-1R | R-0.5R | R-0.1R | R-0.05R | R-0.01R |
|---|---|---|---|---|---|---|
| 8 | 256 | 987 | 6887.5 | 6030500 | 22978 × 10$^4$ | 2262450 × 10$^6$ |
| 9 | 512 | 2584 | 25705 | 71860 × 10$^3$ | 504475 × 10$^4$ | 2307325 × 10$^8$ |
| 10 | 1024 | 6765 | 95930 | 856275 × 10$^3$ | 1107525 × 10$^5$ | 2353375 × 10$^{10}$ |
| 11 | 2048 | 17711 | 358025 | 1020375 × 10$^4$ | 2431425 × 10$^6$ | 2400150 × 10$^{12}$ |
| 12 | 4096 | 46368 | 1336100 | 1215825 × 10$^5$ | 5338250 × 10$^7$ | 2447850 × 10$^{14}$ |

Furthermore, the ladder resistor inaccuracy is less problematic for filter design applications compared with for data converter design. For the data converter, the ladder resistor accuracy sets the limit on an achievable resolution. In the application to design ultra-low power bio-medical active-RC low pass filter, however, resistor inaccuracy results in error in the value of $R_{eq(max)}$. This problem is not different than using normal passive resistors. The simulation results confirm that the percentage of error of $R_{eq(max)}$ is equal to the percentage of error in the passive resistors forming the ladder. In integrated circuits, automatic tuning circuits are often employed to compensate for inaccurate passive components values.

Figure 3:
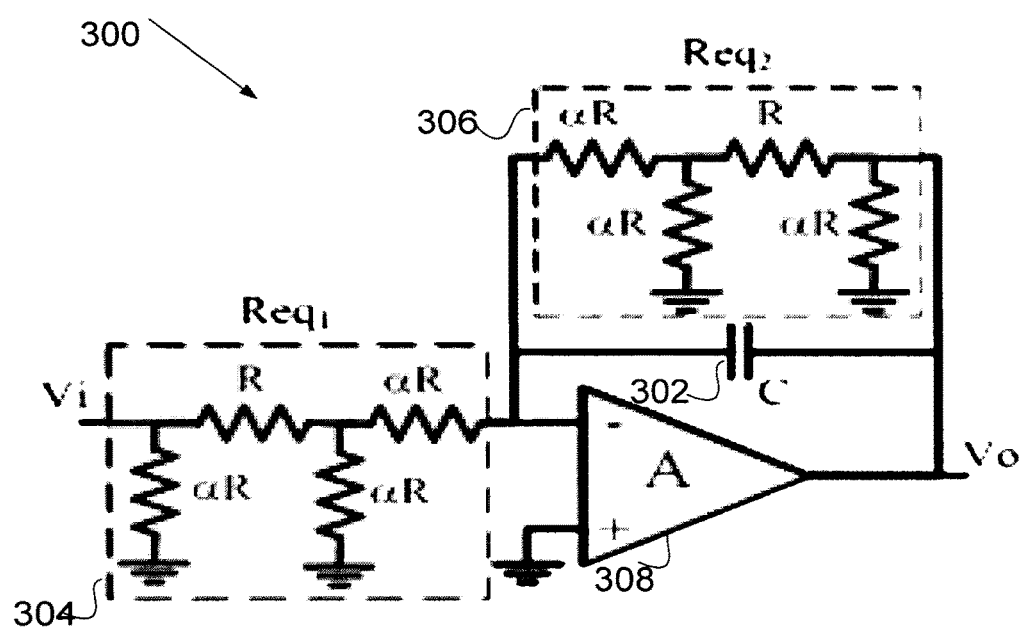
FIG. 3 is an exemplary circuit schematic of an active-RC low-pass filter using a two-stage R-αR ladder.

FIG. 3 is an exemplary schematic of a first order active-RC filter employing two R-αR ladders with 2 stages.

The first order R-αR ladder active-RC low pass filter 300 includes a first input terminal, a first output terminal, a first capacitor 302, a first R-αR ladder network 304, a second R-αR ladder network 306 and a differential operational amplifier 308.

The first R-αR ladder network 304 includes a second input terminal, a second output terminal, a first resistor with a resistance value of R, a second resistor with a resistance value of αR, and a third resistor with a resistance value of αR. A first terminal of the first resistor of R is connected to the first input terminal of the low pass filter 300, and a second terminal of the first resistor is connected to a first terminal of the second resistor and a first terminal of the third resistor. A second terminal of the second resistor is short to the ground, and a second terminal of the third resistor is connected to the second output terminal of the first R-αR ladder network 304.

The second R-αR ladder network includes a third input terminal, a third output terminal, a fourth resistor with a resistance value of R, a fifth resistor with a resistance value of αR, and a sixth resistor with a resistance value of αR. A first terminal of the fourth resistor of R is connected to the third input terminal, and a second terminal of the fourth resistor is connected to a first terminal of the fifth resistor and a first terminal of the sixth resistor. A second terminal of the fifth resistor is short to the ground, and a second terminal of the sixth resistor is connected to the third output terminal of the second R-αR ladder network 306. The third input terminal is connected the first output terminal of the low pass filter 300.

The operational amplifier 308 includes a fourth inverting input terminal, a fifth non-inverting input terminal, and a fourth output terminal. The second output terminal of the first R-αR ladder network 304 and the third output terminal of the second R-αR ladder network 306 are connected to the fourth inverting input terminal. The fifth non-inverting input terminal is shorted to the ground. The first capacitor 302 is connected between the fourth inverting input terminal and the fourth output terminal. The fourth output terminal is connected to the first output terminal of the low pass filter 300.

Theoretical analysis is used to investigate the effect of changing the index and number of stages of R-αR ladder on the circuit performance. The filter exhibits the following transfer function:

$$\frac{V_o}{V_i} = \frac{-1}{sCR\left(2+\alpha+\frac{2+\alpha}{A}\right)+1+\frac{1}{A}\frac{(2+2\alpha)}{\alpha}} \quad (12)$$

wherein $V_i$ is a input voltage of the filter, $V_o$ is a output voltage of the filter, C is the capacitance of the capacitor and A is a gain of the operational amplifier.

Therefore, the gain and pole frequency can be expressed as follows:

$$|A_{o2}| = \frac{1}{1+\frac{1}{A}\frac{(2+2\alpha)}{\alpha}} \quad (13)$$

$$\omega_{o2} = \frac{1+\frac{1}{A}\frac{(2+2\alpha)}{\alpha}}{CR(2+\alpha)\left(1+\frac{1}{A}\right)} \quad (14)$$

Repeating the analysis for the filter of FIG. 3 but assuming three-stage ladders are employed yields the following transfer function:

$$\frac{V_o}{V_i} = \frac{-1}{sCR\left(\frac{2+5\alpha+\alpha^2}{\alpha}+\frac{1}{A}\frac{2+5\alpha+\alpha^2}{\alpha}\right)+1+\frac{2}{A}\frac{(2+5\alpha+\alpha^2)}{\alpha^2}} \quad (15)$$

Therefore, the gain and pole frequency can be expressed as follows:

$$|A_{o3}| = \frac{1}{1+\frac{2}{A}\frac{(2+5\alpha+\alpha^2)}{\alpha^2}} \quad (16)$$

$$\omega_{o3} = \frac{1 + \frac{2}{A}\frac{(2+5\alpha+\alpha^2)}{\alpha^2}}{CR\left(\frac{2+5\alpha+\alpha^2}{\alpha}\right)\left(1+\frac{1}{A}\right)} \quad (17)$$

The two parameters, α, and A, determine the filter's characteristics as shown in equation (12)-(17). For a fixed value of A, as a value of α decreases, an error in the gain of the filter, which the error of the gain of the filter is defined as a variation of the filter's gain, increases. On the other hand, for a fixed value of α, the errors in the filter's gain and pole frequency decrease for higher values of A, wherein the error of the pole frequency is defined as a variation of the pole frequency.

In order to investigate the effects of increasing the number of stages, the error in the filter characteristics for the two stage and three stage filters are calculated. For example, the errors in $|A_{o2}|$ and $\omega_{o2}$ are about 0.2% with the A of 100 dB and α of 0.01. However, for the same values of A and α, errors in $|A_{o3}|$ and $\omega_{o3}$ become 16.7% and 20.6%, respectively. Therefore, as the number of stages is increased, the error in the filter characteristics drastically increases. Consequently, higher operational amplifier gain is required to compensate for the increased errors.

Analysis and consequently expressions of (15) through (17) becomes more sophisticated as the number of stages is increased. The gains and pole frequencies are determined form simulation results through the ac responses. The operational amplifier is modeled with voltage dependent voltage source with a gain of 100 dB while C=10 pF, and base resistance of R=40 kΩ for the ladders are adopted. The obtained data showing the effect of a on gain and the minimum pole frequency achievable by the filter are given in Table II. The results of Table II are plotted in FIG. 4.

minimum achievable pole frequency initially starts decreasing with the value of a but then it saturates. Consequently, R-0.05R and R-0.01R ladder families do not provide good results. On the other hand, attractive results that provide minimum frequency with minimum gain error are highlighted with bold font and asterisks within Table II. These cases are further studied and their relative areas are compared in Table III. Table III lists several attractive results obtained from Table I.

The total area of various options is calculated in terms of the area of the base resistance (Area_R). Given that the total area of 12-stage R-2R ladder is 35×Area_R with a pole frequency of 100 Hz, Table III shows that employing a 11-stage R-0.5R ladder would decrease the pole frequency from 100 Hz of R-2R ladder to 10 Hz while providing area saving of about 56% compared with its counterpart of R-2R ladders. Also, the areas are normalized in reference to the minimum possible pole frequency of 10 Hz as the various options have different pole frequencies. For example, the base resistance and Area_R for the case of 12 stage R-1R need to be increased by a factor of 14/10 in order to shift the pole frequency from 14 Hz to 10 Hz. According to Table III, it clear that the 11 stage R0.5R is the optimum solution as it achieves the lowest possible frequency with minimum area. Furthermore, the relative area saving by using R-0.5R to R-2R is 95.6% rather than 56%. Decreasing the pole frequency from 100 Hz to 10 Hz requires scaling up the base resistance of the R-2R by the same factor leading to actual area of 3500×Area_R. This means that R-0.5R would actually require 4.4% of the R-2R ladders to achieve the same pole frequency. Unlike for the case of notch filter design, in which the error must be maintained very small to 0 dB in order to achieve notch response with acceptable depth, in the case of low pass filter the error results in attenuation. For the case of notch response, the only solution to compensate for

TABLE II

Results for operational amplifier gain of A = 100 dB, C = 10 pF and R = 40 kΩ.

| | | Stages | | | | | | | | |
|---|---|---|---|---|---|---|---|---|---|---|
| | | 4 | 5 | 6 | 7 | 8 | 9 | 10 | 11 | 12 |
| R2R | Gain | 0 dB | 0 dB | 0 dB | 0 dB | 0 dB | 0 dB | 0 dB | 0 dB | 0 dB |
| | fo | 24.5 kHz | 12.4 kHz | 6.2 kHz | 3.1 kHz | 1.6 kHz | 800 Hz | 400 Hz | 200 Hz | 100 Hz |
| R-1R | Gain | 0 dB | 0 dB | 0 dB | 0 dB | -0.1 dB | -0.3 dB | -0.7 dB | -1.7 dB | -4 dB* |
| | fo | 20 kHz | 7.2 kHz | 7.2 kHz | 1 kHz | 400 Hz | 160 Hz | 65 Hz | 27 Hz | 14 Hz* |
| R-0.5R | Gain | 0 dB | 0 dB | -0.1 dB | -0.3 dB | -1 dB | -4 dB | -10 dB* | -19 dB* | -30 dB |
| | fo | 11 kHz | 3 kHz | 800 Hz | 220 Hz | 66 Hz | 24 Hz | 14 Hz* | 10 Hz* | 10 Hz |
| R-0.1R | Gain | -0.3 dB | -3 dB | -15 dB | -35 dB | -56 dB | -78 dB | -99 dB | -120 dB | -142 dB |
| | fo | 1.4 kHz | 116 Hz | 56 Hz | 32 Hz | 40 Hz | 40 Hz | 40 Hz | 40 Hz | 41 Hz |
| R-0.05R | Gain | -1.7 dB | -15 dB | -40 dB | -67 dB | -94 dB | -120 dB | -147 dB | -174 dB | -200 dB |
| | fo | 500 Hz | 108 Hz | 85 Hz | 90 Hz | 80 Hz | 80 Hz | 80 Hz | 80 Hz | 70 Hz |
| R-0.01R | Gain | -27 dB | -67 dB | -107 dB | -147 dB | -187 dB | -227 dB | -267 dB | -308 dB | -348 dB |
| | fo | 440 Hz | 430 Hz | 450 Hz | 390 Hz | 370 Hz | 370 Hz | 385 Hz | 425 Hz | 450 Hz |

TABLE III

Several attractive results obtained from Table I.

| Frequency | Error | Designs | Area/Area_R | Scaled for 10 Hz pole |
|---|---|---|---|---|
| 10 Hz | -19 dB | 11 stage R0.5R | 15.5/35 | 15.5 |
| 14 Hz | -4 dB | 12 stage R1R | 23/35 | 32.2 |
| 14 Hz | -10 dB | 10 stage R0.5R | 14/35 | 19.6 |

Figure 4A:
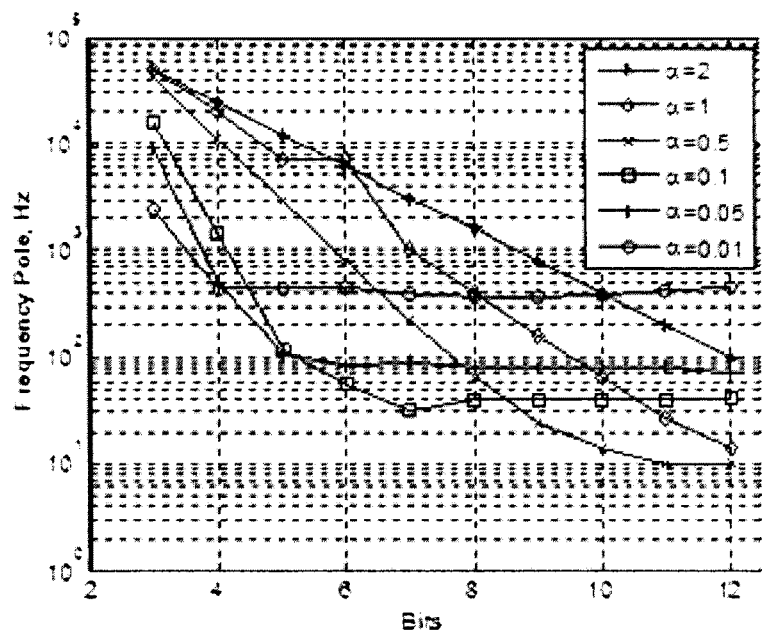
FIG. 4A is graph of pole frequencies of the active-RC low-pass filter as a function of a in various R-αR ladders using an operational amplifier with a gain of 100 dB.
Figure 4B:
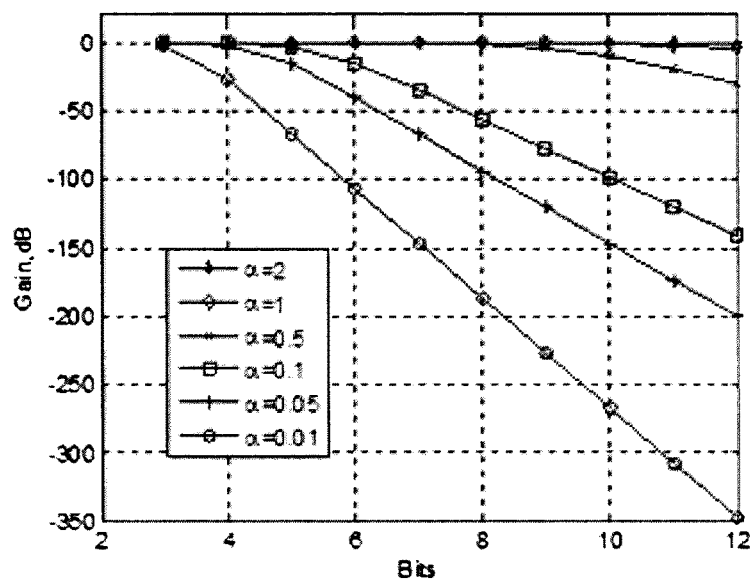
FIG. 4B is graph of gains of the active-RC low-pass filter as a function of a in various R-αR ladders using an operational amplifier with a gain of 100 dB.

As table II and FIG. 4 show that as the value of a is decreased, the gain error increases. On the other hand, the the error is to increase the gain of the operational amplifier gain. However, for the case of the low-pass filter, the error can be reduced by adjusting the value of input resistor without significantly increasing the gain of the operational amplifier gain. Assuming the operational amplifier has sufficiently large gain A, the filter transfer function would be given by:

$$\frac{V_o}{V_i} = \frac{-R_{eq2}/R_{eq1}}{sCR_{eq2}+1} \quad (18)$$

wherein $R_{eq1}$ is an equivalent resistance of the first R-αR ladder 304, and $R_{eq1}$ is an equivalent resistance of the second R-αR ladder 306. Hence the gain can be adjusted via varying $R_{eq1}$ without disturbing the pole frequency. In other words, $R_{eq1}$ can be arbitrarily programmed to adjust the gain to its desired value. The gain of the operational amplifier is usually not known a-priori. Hence an automatic gain control circuit can be used if desired to adjust the filter gain to a pre-specified setting.

Figure 5A:
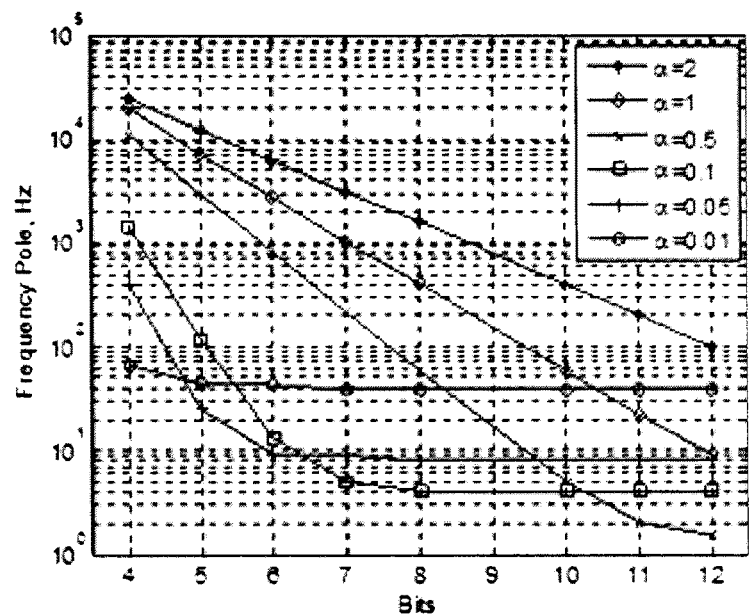
FIG. 5A is graph of pole frequencies of the active-RC low-pass filter as a function of a in various R-αR ladders using an operational amplifier with a gain of 120 dB.
Figure 5B:
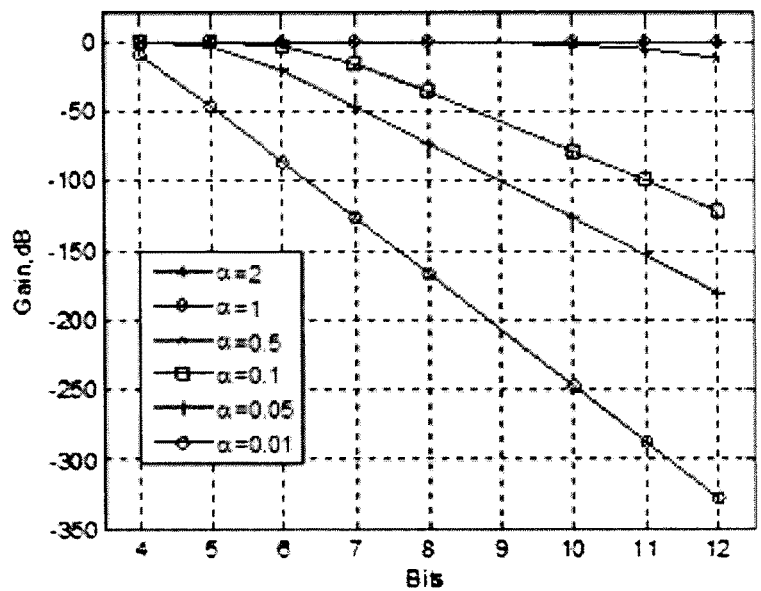
FIG. 5B is a graph of gains of the active-RC low-pass filter as a function of a in various R-αR ladders using an operational amplifier with a gain of 120 dB.

A similar analysis is repeated for an operational amplifier with 120 dB gain. The results are summarized in Table IV. The results of Table IV are plotted in FIG. 5. It is clear that higher operational amplifier gain results in reduced gain error and lower pole frequency. Table IV shows that the results provided by R-0.05R and R-0.01R ladders are not attractive as they lead to minimum frequency of 8 Hz and 38 Hz, respectively. In addition, these cases are associated with huge gain errors. On the other hand, there are several attractive results demonstrated by R-1R, R-0.5R and R-0.1R ladders. The best possible options are shown with bold font and asterisks providing very low pole frequency with minimum gain error. Table V gives a summary and comparison of these attractive results.

According to Table V, it clear that the 12-stage R-0.5R is the optimum solution as it achieves the lowest possible frequency with minimum area.

Figure 6:
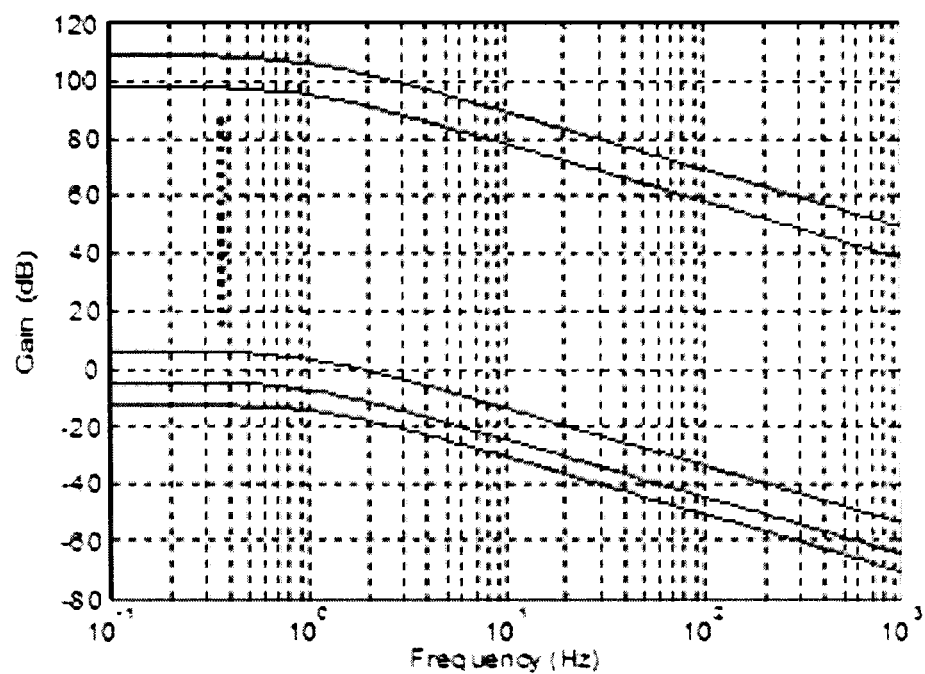
FIG. 6 is a graph of gain tuning of the active-RC low-pass filter.

In order to compensate for gain error, it is required to program the ladder forming $R_{eq1}$. Similar to the R-2R used in data converter, it is assumed that there are 12 switches. Each switch is in series with one of the α-Resistor. The switch is used to either connect the resistor to ground or to input of the operational amplifier. Simulation results showing gain adjustments as suggested by (4) via varying $R_{eq1}$ are obtained. FIG. 6 shows simulation results demonstrating gain adjustments from −12 dB (when the digital world for input resistor is 000000000001), to 110 dB (when the digital world for $R_{eq1}$ is 111111111111). The 12-bit digital word represents the controlling voltages of the switches with "1" meaning that the resistor is connected to the operational amplifier. Table VI gives ranges of gain adjustment for the options listed in Table V. The selected option of the 12-stage R-0.5R demonstrates the highest possible corrections range then followed by the case of 7-stage R-0.1R option. Therefore, wide gain tuning range is an additional advantage of the selected design.

TABLE IV

Results for opamp gain of A = 120 dB, C = 10 pF and R = 40 kΩ.

| | | Stages | | | | | | | |
|---|---|---|---|---|---|---|---|---|---|
| | | 4 | 5 | 6 | 7 | 8 | 10 | 11 | 12 |
| R-2R | Gain | 0 dB | 0 dB | 0 dB | 0 dB | 0 dB | 0 dB | 0 d | 0 dB |
| | fo | 24.5 kHz | 12.4 kHz | 6.2 kHz | 3.1 kHz | 1.6 kHz | 400 Hz | 200 Hz | 100 Hz |
| R-1R | Gain | 0 dB | 0 dB | 0 dB | 0 dB | 0 dB | −0.1 dB | −0.2 dB | −0.5 dB* |
| | fo | 20 kHz | 7.2 kHz | 2,75 kHz | 1 kHz | 403 Hz | 58 Hz | 22 Hz | 9 Hz* |
| R-0.5R | Gain | 0 dB | 0 dB | 0 dB | 0 dB | −0.1 dB | −1.7 dB* | −5 dB* | −12.3 dB* |
| | fo | 11 kHz | 3 kHz | 812 Hz | 215 Hz | 58 Hz | 5 Hz* | 2 Hz* | 1.5 Hz* |
| R-0.1R | Gain | 0 dB | −0.3 dB | −3 dB* | −16 dB* | −36 dB | −79 dB | −100 dB | −122 dB |
| | fo | 1.4 kHz | 116 Hz | 13 Hz* | 5 Hz* | 4 Hz | 4 Hz | 4 Hz | 4 Hz |
| R-0.05R | Gain | −0.1 dB | −3 dB | −21 dB | −47 Hz | −74 dB | −127 dB | −154 dB | −181 dB |
| | fo | 400 Hz | 25 Hz | 9 Hz | 9 Hz | 8 Hz | 8 Hz | 8 Hz | 8 Hz |
| R-0.01R | Gain | −10 dB | −47 dB | −87 dB | −127 dB | −167 dB | −248 dB | −288 dB | −328 dB |
| | fo | 65 Hz | 44 Hz | 42 Hz | 38 Hz | 38 Hz | 38 Hz | 38 Hz | 38 Hz |

TABLE V

Several attractive results obtained from Table III.

| Frequency | Error | Designs | Area/Area_R | Scaled for 1.5 Hz pole |
|---|---|---|---|---|
| 1.5 Hz | −12.3 dB | 12 stage R-0.5R | 17 | 17 |
| 2 Hz | −5 dB | 11 stage R-0.5R | 15.5 | 20.7 |
| 5 Hz | −1.7 dB | 10 stage R-0.5R | 14 | 46.7 |
| 5 Hz | −16 dB | 7 stage R-0.1R | 6.7 | 22.3 |
| 9 Hz | −0.5 dB | 12 stage R-1R | 23 | 138 |
| 13 Hz | −3 dB | 6 stage R0.1R | 5.6 | 48.5 |

TABLE VI

Ranges of gain adjustment.

| Option | Gain tuning |
|---|---|
| 12 stage R-0.5R | −12 dB to 110 dB |
| 11 stage R-0.5R | −5 dB to 103 dB |
| 10 stage R-0.5R | −1.7 dB to 95 dB |
| 7 stage R-0.1R | −16 dB to 101 dB |
| 12 stage R-1R | −0.5 dB to 88 dB |
| 6 stage R-0.1R | −3 dB to 90 dB |

For example, Table V suggests that employing a 12 stage R-0.5R ladder would decrease the pole frequency from 100 Hz of R-2R ladder to 1.5 Hz while providing area saving of 50% compared with its counterpart of R-2R ladders. However, in order to decrease the pole frequency from 100 Hz to 1.5 Hz, the base resistance of the R-2R must be scaled up by same factor leading to area of 2333×Area_R. This means that R-0.5R would actually provide an area saving of 99.3% or equivalently require 0.7% of the R2R ladders to achieve the same pole frequency. Therefore, all areas are normalized in reference to the minimum possible pole frequency of 1.5 Hz as the various options have different pole frequencies. For example, the base resistance and Area_R for the case of 11-stage R-0.5R should be increased by a factor of 2/1.5 in order to shift the pole frequency from 2 Hz to 1.5 Hz.

A fully differential second-order low pass Tow-Tomas filter was fabricated in 0.18 μm CMOS process. The filter shown in FIG. 7A employs inverting integrators like the first-order filter of FIG. 3. But it can be designed for arbitrary pole quality factor unlike cascading of two first-order sections.

Figure 7A:
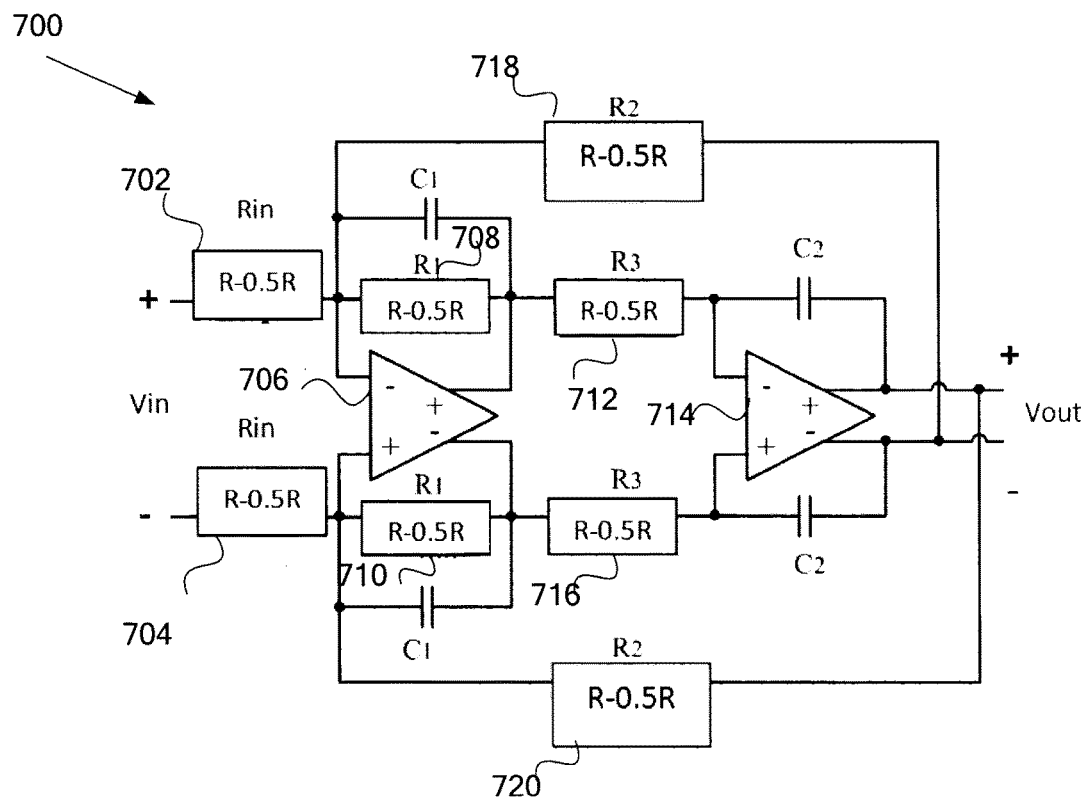
FIG. 7A is an exemplary schematic of a fully differential Tow-Thomas biquad filter employing R-0.5R ladders.

As FIG. 7A shows that the disclosed fully differential second-order low-pass Tow-Tomas filter 700 includes a non-inverting input terminal, a inverting input terminal, a non-inverting output terminal and a inverting output terminal, two differential operational amplifiers, eight R-0.5R ladder circuits, and four capacitors.

A first R-0.5R ladder circuit 702 is connected between the non-inverting input terminal of the filter 700 and an inverting input terminal of a first operational amplifier 704. A second R-0.5R ladder circuit 706 is connected between the inverting input terminal of the filter 700 and a non-inverting input terminal of the first operational amplifier 704. A third R-0.5R ladder circuit 708 and a first capacitor are connected between the inverting input terminal and a non-inverting output terminal of the first operational amplifier 706. A fourth R-0.5R ladder circuit 710 and a second capacitor are connected between the non-inverting input terminal and a inverting output terminal of the first operational amplifier 706.

A fifth R-0.5R ladder circuit 712 is connected between the non-inverting output terminal of the first operational amplifier 706 and an inverting input terminal of a second operational amplifier 714. A sixth R-0.5R ladder circuit 716 is connected between the inverting output terminal of the first operational amplifier 706 and a non-inverting input terminal of the second operational amplifier 714. A seventh R-0.5R ladder circuit 718 is connected between the inverting input terminal of the first operational amplifier 706 and the inverting output terminal of the second operational amplifier 714. A eighth R-0.5R ladder circuit 720 is connected between the non-inverting input terminal of the first operational amplifier 706 and the non-inverting output terminal of the second operational amplifier 714. The non-inverting output of the second operational amplifier 714 is connected to the non-inverting output of the filter 700. The inverting output of the second operational amplifier 714 is connected to the inverting output of the filter 700. A third capacitor is connected between the inverting input terminal and non-inverting output terminal of the second operational amplifier 714. A fourth capacitor is connected between the non-inverting input terminal and inverting output terminal of the second operational amplifier 714.

Figure 7B:
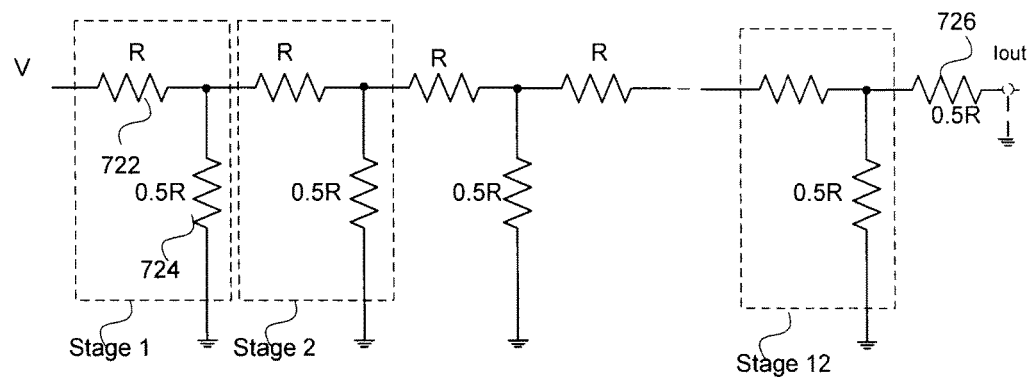
FIG. 7B is an exemplary schematic of a R-0.5 ladder used in the Tow-Thomas biquad filter.

FIG. 7B shows a 12-stage R-0.5R ladder that is used in the filter 700. It includes 12 stages of resistance network. Series and shunt resistance network are arranged in cascade to generate a voltage to current conversion. The series resistors 722 of the stages from 1 to 12 have a resistance of R. The terminal resistor 726 has a resistance of 0.5 R. The shunt resistors 724 for all the stages have a resistance of 0.5R, with a first terminal of each shunt resistor 724 being connected to the series resistor 722 in the same stage, and a second terminal of each shut resistor being connected to the ground.

The disclosed design adopts 12-stage R-0.5R ladders with R=40 kΩ for the first R-0.5R ladder 702, the second R-0.5R ladder 704, the fifth R-0.5R ladder 712, the sixth R-0.5R ladder 714, the seventh R-0.5R ladder 718, and the eighth R-0.5R ladder 720, R=28.3 k for the third R-0.5R ladder 708 and the fourth R-0.5R ladder 710, and C=10 pF for all the capacitors in order to achieve Butterworth response with 1.5 Hz pole frequency.

Figure 8:
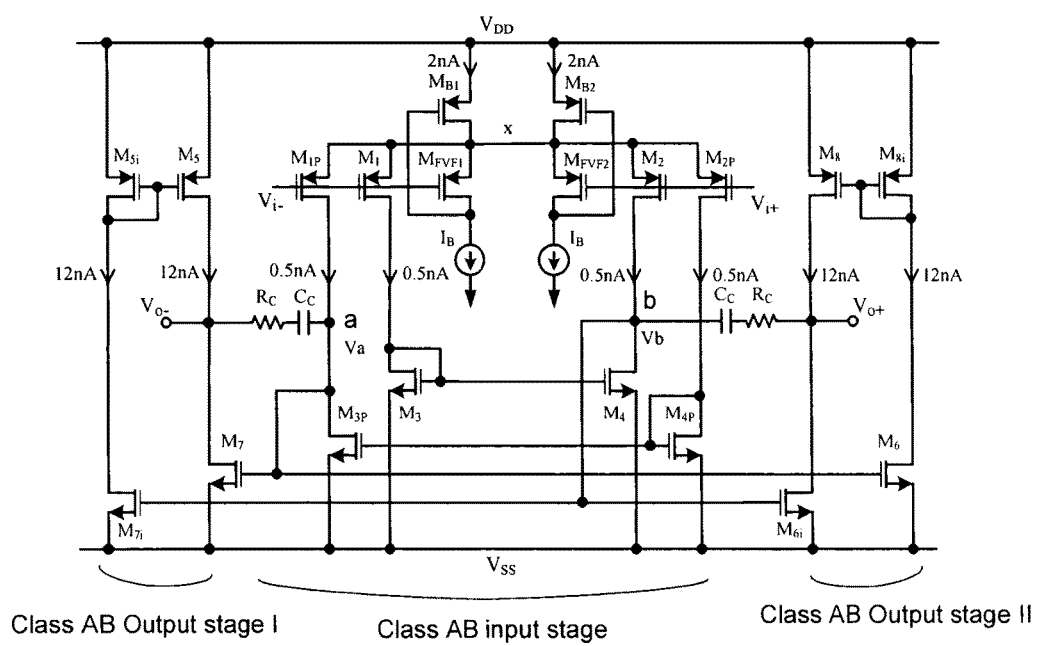
FIG. 8 is an exemplary schematic of a fully differential operational amplifier the disclosed fully differential Tow-Thomas biquad filter.

The filter incorporates two low power operational amplifiers used shown in FIG. 8. The operational amplifier was redesigned in 0.18 μm technology using supply voltages of ±0.9V. The operational amplifier was optimized to achieve of 120 dB with a total current of about 52 nA. Capacitor arrays are utilized to allow tuning of ±20% around the nominal pole frequency.

Two stage op-amps have rail-to-rail output swing and can drive both resistive and capacitive loads. Class AB two stage op-amps are designed using a stage class AB at the input or at the output. However, in this paper a new design strategy where both stages (input and output) are working in class AB is employed. It has been coined as class AB/AB op-amps and delivers high current peaks with small quiescent currents.

The two stage class AB/AB amplifier, illustrated in FIG. 8, is used to build the low-pass filter. The fully-differential topology consists of two class AB stages. The input stage includes the transistors $M_1$-$M_4$, $M_{1P}$-$M_{2P}$, $M_{FvF1-2}$, and $M_{B1}$-$M_{B2}$. Two Flipped Voltage Followers (FVF) are formed by the transistors $M_{FvF1}$-$M_{FvF2}$ and the two current sources to generate a very low impedance at the common source node x of transistors $M_1$, $M_2$, $M_{1P}$, $M_{2P}$, and $M_{FvF1}$-$M_{FvF2}$. The two current sources provide bias currents with a value of $I_{bias}$. The node x follows the maximum value of the input voltages $V_{i-}$, $V_{i+}$ through a level shift of VSG of the transistors $M_1$, $M_2$, $M_{1P}$, $M_{2P}$, and $M_{FvF1}$-$M_{FvF2}$. The transistors $M_1$, $M_2$, $M_{1P}$ and $M_{2P}$ have the same width and length, and therefore the quiescent current $I_{D1}$ in M1-M2 and the quiescent current $I_{D2}$ in $M_{1P}$-$M_{2P}$ are equal to $I_{bias}$. By application of a large differential input voltage, the dynamic currents $I_{D1}$, $I_{D2}$ that are essentially larger than $I_{bias}$, are generated. The Transistors M3, M4, M3P, M4P form current mirrors and generate complementary currents at nodes "a" and "b". As none of the transistors $M_1$, $M_2$, $M_{1P}$, $M_{2P}$ are driven to cutoff region when a differential signal is applied, this circuit can achieve high speed and low distortion.

The class AB operational amplifier output stage does not require a separate quiescent current control circuit to operate at very low supply voltages $V_{DDmin}=V_{GS}+V_{DSsat}$, and has rail-to-rail output swing. The quiescent gate-source voltage at the output nodes of the first stage (Va and Vb) corresponds to the quiescent gate-source voltage of $M_3$, $M_4$, $M_{3P}$ and $M_{4P}$. This value sets the quiescent current in the output stage formed by the transistors $M_5$-$M_8$ and $M_{5i}$-$M_{8i}$. The output section I includes the transistors $M_5$, $M_{5i}$, $M_7$ and $M_{7i}$. The output section II includes the transistors $M_6$, $M_{6i}$, $M_8$ and $M_{8i}$. The operation of the output section I is analyzed. The transistors M7, M7i and M5, M5j are transistors with a same width and length. Under quiescent conditions the voltages $V_a=V_b=V_{GS3}=V_{GS4}$ lead to equal currents in M7 and M7i, wherein $I_{D7}=I_{D7i}=I_{bias}*((W/L)_7/(W/L)_3)$. Since $M_5$ and $M_{5i}$ form a unity gain current mirror, the quiescent current $I_{D5}$ in M5 has the same value $I_{D7}$ as in $M_7$, and zero output current results under the quiescent conditions. For positive variations in $V_a$ (and corresponding negative variations in $V_b$) the current in $M_7$ increases while that in $M_{7j}$ decreases. This leads to a negative output current $I_{out}$ at the terminal $V_{O-}$. The value of the output currents $I_{out}$ can be essentially larger than the quiescent drain current of the transistors $M_7$ and $M_5$. Operation of the section II is identical but in this case an equal valued positive output current $I_{out}$ is generated at $V_{O+}$. The output stage can deliver large dynamic output currents, to the external terminal of a compensation capacitors Cc and a load capacitors $C_L$.

Figure 9:
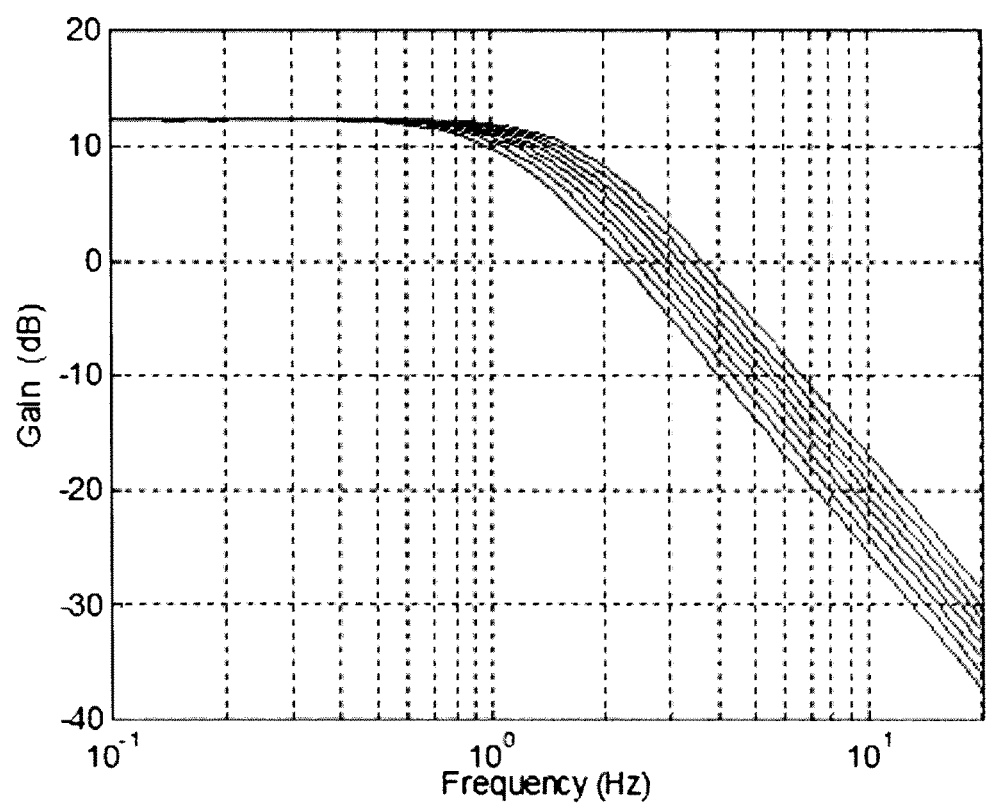
FIG. 9 is a graph of magnitude response of the disclosed a fully differential Tow-Thomas biquad filter employing the disclosed a fully differential operational amplifier employed in the disclosed.

Experimental results showing the magnitude response of the filter with tuning around 1.5 Hz are shown in FIG. 9. In order to compensate for gain error, the ladders forming the resistors Rin are to obtain cutoff frequency as low as 1 Hz. The output noise spectral density was found to be approximately 39 μV/Hz1/2. This leads to total input noise of about 12 μV. As the passive resistors $R_{eq(max)}$ of the ladders increases, the noise spectral density increases. The linearity has been measured through applying sinusoidal inputs. The amplitude is varied until total harmonic distortion (THD) of 40 dB is obtained with an input amplitude of 0.15V (RMS of 0.11V). The corresponding 40 dB THD dynamic range DR=79 dB. Comparison with several available solutions, the disclosed provides significant improvement in the DR over all others. The filter consumes significantly much less power consumption compared with its counterpart described in S. Solis-Bustos, J. Silva-Martinez, F. Maloberti, and E. Sanchez-Sinencio, ("A 60 dB dynamic-range CMOS sixth-order 2.4 Hz low-pass filter for medical applications," IEEE Trans. Circuits Syst. II, vol. 47, no. 12, pp. 1391-1398, December 2000—incorporated herein by reference) and C. Chen, P. Mak, T. Zhang, M. Vai, P. Mak, S. Pun, F. Wan, R. P. Martins, ("A 2.4 Hz-to-10 kHz-tunable biopotential filter using a novel capacitor multiplier," Asia Pacific Conference on Postgraduate Research in Microelectronics & Electronics (PrimeAsia 2009), China, pp. 372-375, January 2009—incorporated herein by reference). The disclosed filter consumes about twice the power of S. Lee, and C. Cheng, ("Systematic design and modeling of a OTA-C filter for portable ECG detection," *IEEE Tran. on Biomed. Circ. and Syst.*, vol. 3, no. 1, pp. 53-64, February 2009—incorporated herein by reference) and C. L. Hsu, M. H. Ho, Y. K. Wu, and T. H. Chen, "Design of low frequency low-pass filters for biomedical applications," in *Proc. Asia Pacific Conf. IEEE Circuits Systems*, Singapore, 2006, pp. 690-695—incorporated herein by reference), but it obtains less pole frequency. Moreover, the disclosed low pass filter is a more area efficient compared with the other ones.

Active R-2RC approach provides high linear and low power design solution for implementing low frequency filters employed by fully integrated biomedical applications. However, its main drawback is the large area occupied by the ladder at low operational frequency range within few tens of Hz. The disclosure shows that the R-0.5R ladders provide more area efficient solution leading to the implementation of lower pole frequencies. R-0.5R ladders allow the design of a low pass filter with 1 Hz pole frequency instead of 100 Hz while requiring less than 50% of the area. And the area saving is much more when calculated for a given pole frequency. The R-0.5R ladders would actually needs 0.7% silicon of the R-2R ladders counterpart for realizing a given pole frequency. The R-2R ladders are described in U.S. Pat. No. 8,436,679, the contents of which are incorporated herein by reference. Experimental results show that the disclosed filter exhibits better dynamic range compared with the available solution while consuming comparable power consumption.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A R-0.5R ladder active-RC low pass filter with reduced pole frequencies and chip area for a high linear and low power bio-medical applications, comprising:
    a first inverting input terminal;
    a second non-inverting input terminal;
    a first inverting output terminal;
    a second non-inverting output terminal;
    first and second operational amplifiers connected together in a Tow-Thomas biquadratic filter circuit;
    a first R-0.5R ladder circuit connected between the first non-inverting input terminal of the low-pass filter and a third inverting input terminal of the first operational amplifier;
    a second R-0.5R ladder circuit connected between the second inverting input terminal of the low-pass filter and a fourth non-inverting input terminal of first operational amplifier;
    a third R-0.5R ladder circuit connected in parallel with a first capacitor, wherein the third R-0.5R ladder circuit is connected between the third inverting input terminal and a third non-inverting output terminal of the first operational amplifier;
    a fourth R-0.5R ladder circuit connected in parallel with a second capacitor, wherein the fourth R-0.5R ladder is connected between the fourth non-inverting input terminal and a fourth inverting output terminal of the first operational amplifier;
    a fifth R-0.5R ladder circuit connected between the third non-inverting output terminal of the first operational amplifier and a fifth inverting input terminal of a second operational amplifier;
    a sixth R-0.5R ladder circuit connected between the fourth inverting output terminal of the first operational amplifier and a sixth non-inverting input terminal of the second operational amplifier;
    a seventh R-0.5R ladder circuit connected between the third inverting input terminal of the first operational amplifier and a sixth inverting output terminal of the second operational amplifier, wherein the sixth inverting output terminal is connected to the second inverting output terminal of the low-pass filter; and
    an eighth R-0.5R ladder circuit connected between the fourth non-inverting input terminal of the first and a fifth non-inverting input terminal of the second operational amplifier, wherein the fifth non-inverting output terminal is connected to the first non-inverting output terminal of the low-pass filter.

2. The filter of the claim 1, wherein the first, second, third, fourth, fifth, sixth, seventh and eighth R-0.5R ladder networks comprising:
    at least one R-0.5R resistor stage of the first, second, third, fourth, fifth, sixth, seventh and eighth R-0.5R ladder circuits arranged in cascade, and including:
        a first resistor stage having an input, and an output,
        a final stage having a series connected terminal resistor have a resistance of 0.5R;
        at least one intermediate resistor stage disposed in the cascade between the first resistor stage and the final stage having an input and an output, the output of the intermediate stage feeding in an output-to-input manner through the cascade, wherein the first resistor stage and each intermediate resistor stage includes a series resistor with a resistance of R connected between the input and output terminal of the resistor stage, and a shunt resistor with a resistance of 0.5R connected between the output terminal of the resistor stage and a ground node.

3. The filter of the claim 2, wherein the filter having an α value of 0.5 reduces a silicon area occupied by the filter, compared with the filter having other α values that is greater than 0.5 to implement the filter at a given pole frequency.

4. The filter of the claim 2, wherein the filter having an α value of 0.5 provides improvement in selectivity characteristics while consuming comparable power consumption, compared with another filter having another α value.

5. The filter of the claim 2, wherein equivalent maximum resistances of 2-stage, 3-stage, 4-stage, 5-stage, 6-stage, 7-stage, 8-stage, 9-stage, 10-stage, 11-stage and 12-stage R-αR ladder networks are set as:

$$R_{eq}(2\text{-stages}) = (1+0.5\alpha)2R$$

$$R_{eq}(3\text{-stages}) = (1 + 2.5\alpha + 0.5\alpha^2)\frac{2R}{\alpha}$$

$$R_{eq}(4\text{-stages}) = [1 + 4.5\alpha + 4.5\alpha^2 + 0.5\alpha^3]\frac{2R}{\alpha^2}$$

$$R_{eq}(5\text{-stages}) = [1 + 6.5\alpha + 12.5\alpha^2 + 7\alpha^3 + 0.5\alpha^4]\frac{2R}{\alpha^3}$$

$$R_{eq}(6\text{-stages}) = [1 + 8.5\alpha + 24.5\alpha^2 + 27.5\alpha^3 + 10\alpha^4 + 0.5\alpha^5]\frac{2R}{\alpha^4}$$

$$R_{eq}(7\text{-stages}) = [1 + 10.5\alpha + 40.5\alpha^2 + 70\alpha^3 + 52.5\alpha^4 + 13.5\alpha^5 + 0.5\alpha^6]\frac{2R}{\alpha^5}$$

$$R_{eq}(8 - \text{stages}) = [1 + 12.5\alpha + 60.5\alpha^2 + 142.5\alpha^3 + 168\alpha^4 + 91\alpha^5 + 17.5\alpha^6 + 0.5\alpha^7]\frac{2R}{\alpha^6}$$

$$R_{eq}(9 - \text{stages}) = [1 + 14.5\alpha + 84.5\alpha^2 + 253\alpha^3 + 412.5\alpha^4 + 357\alpha^5 + 147\alpha^6 + 22\alpha^7 + 0.5\alpha^8]\frac{2R}{\alpha^7}$$

$$R_{eq}(10 - \text{stages}) = [1 + 16.5\alpha + 112.5\alpha^2 + 409.5\alpha^3 + 858\alpha^4 + 1039.5\alpha^5 + 693\alpha^6 + 225\alpha^7 + 27\alpha^8 + 0.5\alpha^9]\frac{2R}{\alpha^8}$$

$$R_{eq}(11 - \text{stages}) = [1 + 18.5\alpha + 144.5\alpha^2 + 620\alpha^3 + 1592.5\alpha^4 + 2502.5\alpha^5 + 2359.5\alpha^6 + 1254\alpha^7 + 330\alpha^8 + 32.5\alpha^9 + 0.5\alpha^{10}]\frac{2R}{\alpha^9}$$

$$R_{eq}(12 - \text{stages}) = [1 + 20.5\alpha + 180.5\alpha^2 + 892.5\alpha^3 + 2720\alpha^4 + 5278\alpha^5 + 6506.5\alpha^6 + 4933.5\alpha^7 + 2145\alpha^8 + 467.5\alpha^9 + 38.5\alpha^{10} + 0.5\alpha^{11}]\frac{2R}{\alpha^{10}}$$

wherein $R_{eq}(2\text{-stages})$ is an equivalent maximum resistance of a two-stage R-αR ladder network, $R_{eq}(3\text{-stages})$ is an equivalent maximum resistance of a three-stage R-αR ladder network, $R_{eq}(4\text{-stages})$ is an equivalent maximum resistance of a four-stage R-αR ladder network, $R_{eq}(5\text{-stages})$ is an equivalent maximum resistance of a five-stage R-αR ladder network, $R_{eq}(6\text{-stages})$ is an equivalent maximum resistance of a six-stage R-αR ladder network, $R_{eq}(7\text{-stages})$ is an equivalent maximum resistance of a seven-stage R-αR ladder network, $R_{eq}(8\text{-stages})$ is an equivalent maximum resistance of an eight-stage R-αR ladder network, $R_{eq}(9\text{-stages})$ is an equivalent maximum resistance of a nine-stage R-αR ladder network, $R_{eq}(10\text{-stages})$ is an equivalent maximum resistance of a ten-stage R-αR ladder network, $R_{eq}(11\text{-stages})$ is an equivalent maximum resistance of a eleven-stage R-αR ladder network, and $R_{eq}(12\text{-stages})$ is an equivalent maximum resistance of a eleven-stage R-αR ladder network.

6. The filter of claim 2, wherein the filtering having 12-stage R-0.5R ladders to obtain a lowest operational frequency with a minimum area.

7. A device for biomedical applications comprising:
a filter including
a first inverting input terminal;
a second non-inverting input terminal;
a first inverting output terminal;
a second non-inverting output terminal;
first and second operational amplifiers connected together in a Tow-Thomas biquadratic filter circuit;
a first R-0.5R ladder circuit connected between the first non-inverting input terminal of the low-pass filter and a third inverting input terminal of the first operational amplifier;
a second R-0.5R ladder circuit connected between the second inverting input terminal of the low-pass filter and a fourth non-inverting input terminal of first operational amplifier;
a third R-0.5R ladder circuit connected in parallel with a first capacitor, wherein the third R-0.5R ladder circuit is connected between the third inverting input terminal and a third non-inverting output terminal of the first operational amplifier;
a fourth R-0.5R ladder circuit connected in parallel with a second capacitor, wherein the fourth R-0.5R ladder is connected between the fourth non-inverting input terminal and a fourth inverting output terminal of the first operational amplifier;
a fifth R-0.5R ladder circuit connected between the third non-inverting output terminal of the first operational amplifier and a fifth inverting input terminal of a second operational amplifier;
a sixth R-0.5R ladder circuit connected between the fourth inverting output terminal of the first operational amplifier and a sixth non-inverting input terminal of the second operational amplifier;
a seventh R-0.5R ladder circuit connected between the third inverting input terminal of the first operational amplifier and a sixth inverting output terminal of the second operational amplifier, wherein the sixth inverting output terminal is connected to the second inverting output terminal of the low-pass filter; and
an eighth R-0.5R ladder circuit connected between the fourth non-inverting input terminal of the first and a fifth non-inverting input terminal of the second operational amplifier, wherein the fifth non-inverting output terminal is connected to the first non-inverting output terminal of the low-pass filter.

8. The device of the claim 7, wherein the first, second, third, fourth, fifth, sixth, seventh and eighth R-0.5R ladder networks comprising:

at least one R-0.5R resistor stage of the first, second, third, fourth, fifth, sixth, seventh and eighth R-0.5R ladder circuits arranged in cascade, and including:

a first resistor stage having an input, and an output, a final stage having a series connected terminal resistor have a resistance of 0.5R;

at least one intermediate resistor stage disposed in the cascade between the first resistor stage and the final stage having an input and an output, the output of the intermediate stage feeding in an output-to-input manner through the cascade, wherein the first resistor stage and each intermediate resistor stage includes a series resistor with a resistance of R connected between the input and output terminal of the resistor stage, and a shunt resistor with a resistance of 0.5R connected between the output terminal of the resistor stage and a ground node.

9. The device of the claim 8, wherein the filter having an $\alpha$ value of 0.5 reduces a silicon area occupied by the filter, compared with the filter having other $\alpha$ values that is greater than 0.5 to implement the filter at a given pole frequency.

10. The device of the claim 8, wherein the filter having an $\alpha$ value of 0.5 provides improvement in selectivity characteristics while consuming comparable power consumption, compared with another filter having another $\alpha$ value.

11. The device of the claim 8, wherein equivalent maximum resistances of 2-stage, 3-stage, 4-stage, 5-stage, 6-stage, 7-stage, 8-stage, 9-stage, 10-stage, 11-stage and 12-stage R-$\alpha$R ladder networks are set as:

$$R_{eq}(2\text{-stages}) = (1+0.5\alpha)2R$$

$$R_{eq}(3-\text{stages}) = (1 + 2.5\alpha + 0.5\alpha^2)\frac{2R}{\alpha}$$

$$R_{eq}(4-\text{stages}) = [1 + 4.5\alpha + 4.5\alpha^2 + 0.5\alpha^3]\frac{2R}{\alpha^2}$$

$$R_{eq}(5-\text{stages}) = [1 + 6.5\alpha + 12.5\alpha^2 + 7\alpha^3 + 0.5\alpha^4]\frac{2R}{\alpha^3}$$

$$R_{eq}(6-\text{stages}) = [1 + 8.5\alpha + 24.5\alpha^2 + 27.5\alpha^3 + 10\alpha^4 + 0.5\alpha^5]\frac{2R}{\alpha^4}$$

$$R_{eq}(7-\text{stages}) = [1 + 10.5\alpha + 40.5\alpha^2 + 70\alpha^3 + 52.5\alpha^4 + 13.5\alpha^5 + 0.5\alpha^6]\frac{2R}{\alpha^5}$$

$$R_{eq}(8-\text{stages}) = [1 + 12.5\alpha + 60.5\alpha^2 + 142.5\alpha^3 + 168\alpha^4 + 91\alpha^5 + 17.5\alpha^6 + 0.5\alpha^7]\frac{2R}{\alpha^6}$$

$$R_{eq}(9-\text{stages}) = [1 + 14.5\alpha + 84.5\alpha^2 + 253\alpha^3 + 412.5\alpha^4 + 357\alpha^5 + 147\alpha^6 + 22\alpha^7 + 0.5\alpha^8]\frac{2R}{\alpha^7}$$

$$R_{eq}(10-\text{stages}) = [1 + 16.5\alpha + 112.5\alpha^2 + 409.5\alpha^3 + 858\alpha^4 + 1039.5\alpha^5 + 693\alpha^6 + 225\alpha^7 + 27\alpha^8 + 0.5\alpha^9]\frac{2R}{\alpha^8}$$

$$R_{eq}(11-\text{stages}) = [1 + 18.5\alpha + 144.5\alpha^2 + 620\alpha^3 + 1592.5\alpha^4 + 2502.5\alpha^5 + 2359.5\alpha^6 + 1254\alpha^7 + 330\alpha^8 + 32.5\alpha^9 + 0.5\alpha^{10}]\frac{2R}{\alpha^9}$$

$$R_{eq}(12-\text{stages}) = [1 + 20.5\alpha + 180.5\alpha^2 + 892.5\alpha^3 + 2720\alpha^4 + 5278\alpha^5 + 6506.5\alpha^6 + 4933.5\alpha^7 + 2145\alpha^8 + 467.5\alpha^9 + 38.5\alpha^{10} + 0.5\alpha^{11}]\frac{2R}{\alpha^{10}}$$

wherein $R_{eq}$(2-stages) is an equivalent maximum resistance of a two-stage R-$\alpha$R ladder network, $R_{eq}$(3-stages) is an equivalent maximum resistance of a three-stage R-$\alpha$R ladder network, $R_{eq}$(4-stages) is an equivalent maximum resistance of a four-stage R-$\alpha$R ladder network, $R_{eq}$(5-stages) is an equivalent maximum resistance of a five-stage R-$\alpha$R ladder network, $R_{eq}$(6-stages) is an equivalent maximum resistance of a six-stage R-$\alpha$R ladder network, $R_{eq}$(7-stages) is an equivalent maximum resistance of a seven-stage R-$\alpha$R ladder network, $R_{eq}$(8-stages) is an equivalent maximum resistance of an eight-stage R-$\alpha$R ladder network, $R_{eq}$(9-stages) is an equivalent maximum resistance of a nine-stage R-$\alpha$R ladder network, $R_{eq}$(10-stages) is an equivalent maximum resistance of a ten-stage R-$\alpha$R ladder network, $R_{eq}$(11-stages) is an equivalent maximum resistance of a eleven-stage R-$\alpha$R ladder network, and $R_{eq}$(12-stages) is an equivalent maximum resistance of a eleven-stage R-$\alpha$R ladder network.

12. The device of claim 8, wherein the filtering having 12-stage R-0.5R ladders to obtain a lowest operational frequency with a minimum area.

* * * * *